United States Patent [19]

Ackerman

[11] 4,280,503
[45] Jul. 28, 1981

[54] BIPOLAR ELECTRODE INSERTION APPARATUS

[75] Inventor: Bernard Ackerman, Metuchen, N.J.

[73] Assignee: Electro-Catheter Corporation, Rahway, N.J.

[21] Appl. No.: 122,568

[22] Filed: Feb. 19, 1980

[51] Int. Cl.³ .............................................. A61N 1/00
[52] U.S. Cl. .................................. 128/419 P; 128/784
[58] Field of Search ...................... 128/419 P, 784, 785, 128/788

[56] References Cited

U.S. PATENT DOCUMENTS

| 3,078,850 | 2/1963 | Schein et al. | 128/419P |
| 3,568,660 | 3/1971 | Crites et al. | 128/419 P |
| 3,638,656 | 2/1972 | Grandjean et al. | 128/419 P |
| 3,680,544 | 8/1972 | Shinnick et al. | 128/419 P |
| 4,166,469 | 9/1979 | Littleford | 128/419 P |

*Primary Examiner*—William E. Kamm
*Attorney, Agent, or Firm*—Hubbell, Cohen, Stiefel & Gross

[57] ABSTRACT

A bipolar electrode insertion apparatus (20) in which a common needle (34) is employed for selectively placing both a heart stimulating fluid (62) and a bipolar electrode pair (40) into the heart. Verification of entry into the heart chamber prior to placement of the fluid or bipolar electrode pair (40) in the heart is also provided. The apparatus (20) of the present invention includes a syringe (22) capable of injecting the fluid (62) into the ventricular cavity (60) for restarting the heart function. The needle (34) is a hollow needle having an inlet end and an outlet end for insertion into the heart with a bifurcated chamber (32) being disposed in flow through communication between the syringe (22) outlet end and the needle (34) inlet end. The fluid (62) is selectively injectable into the chamber inlet end (42) through the syringe (22) outlet end and therefrom through the common needle (34) into the ventricular cavity (60) of the heart. The bifurcated chamber (32) contains one branch (42) capable of receiving the fluid (62) from the syringe (22) and another branch (42) comprising an entrance port for a flexible bipolar electrode pair (40) with the entrance port being in flow through communication with the needle (34) inlet end for selective insertion of the bipolar electrode pair (40) through the entrance port into the needle (34) and therefrom through the needle (34) into the ventricular cavity (60). The flexible bipolar electrode pair (40) has a distal end (50) which is preloaded into the needle (34) and a proximal end extending outwardly through a gasket-type seal (54) at the outer end of the entrance port for enabling the selective insertion of the bipolar electrode pair distal end (50) into the ventricular cavity (60).

23 Claims, 7 Drawing Figures

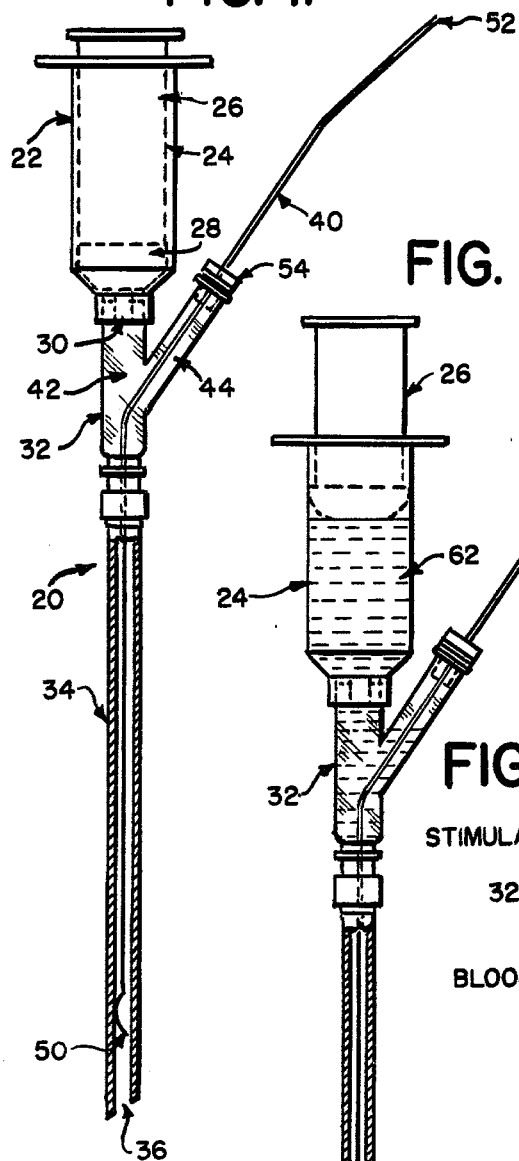
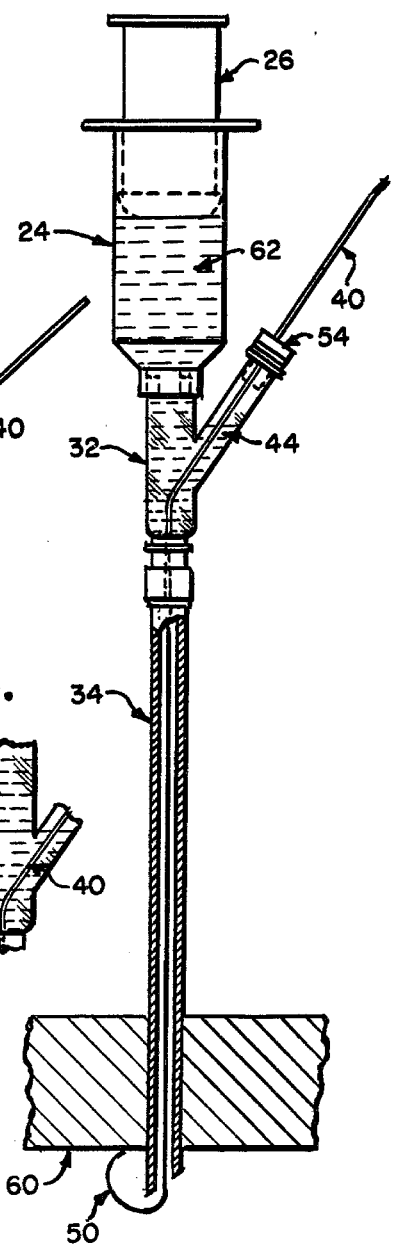
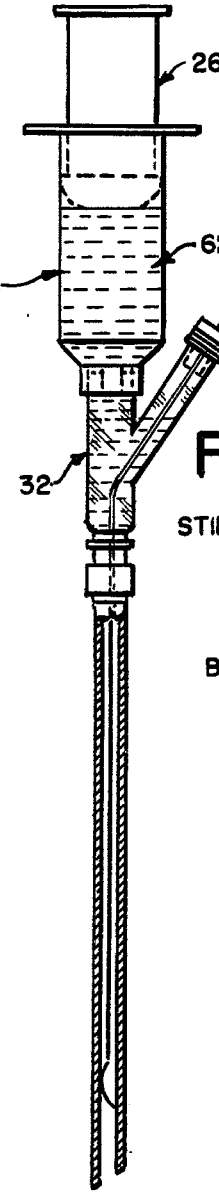
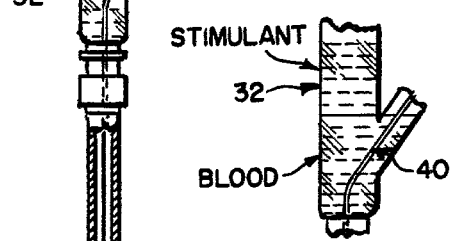

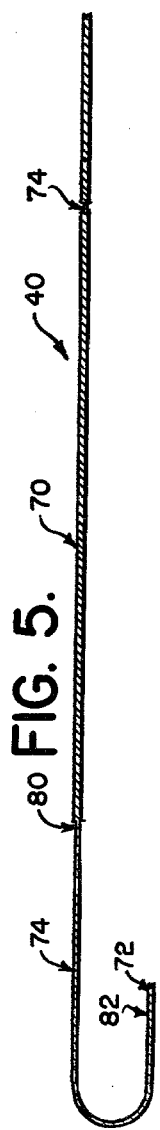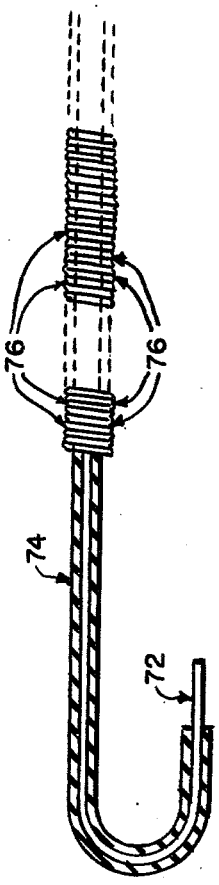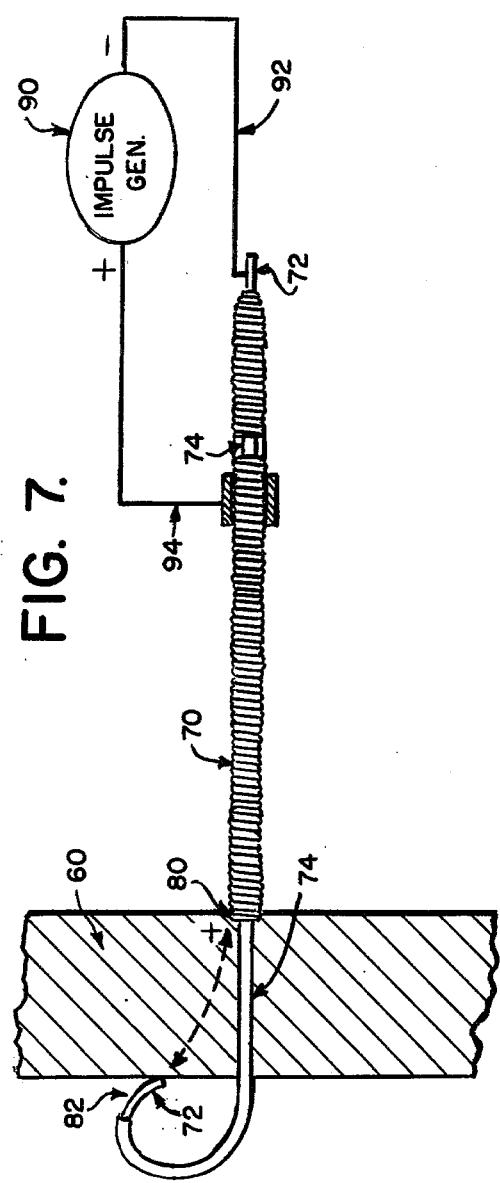

BIPOLAR ELECTRODE INSERTION APPARATUS

TECHNICAL FIELD

The present invention relates to bipolar electrode insertion apparatus.

BACKGROUND ART

The use of bipolar electrodes for insertion into the ventricular cavity for the purpose of restarting the heart function by the transmission thereto of electrical impulses is well known. Such bipolar electrode pairs may comprise a flexible inner conductive element and a flexible outer conductive element fabricated from an extremely flexible and resilient coil spring with an insulating element disposed between the flexible inner and outer conductors and with the outer conductive element having a bend in the form of an elbow at one end thereof. Such a bipolar electrode is disclosed in my previous U.S. Pat. No. 3,516,412. In such a prior art arrangement, the bipolar electrode pair is inserted into the ventricular cavity by puncturing the chest wall and the wall of the heart muscle with a needle. The needle in such a prior art arrangement may comprise a cylindrical sheath or sleeve through which a substantially rigid pointed stylet is inserted to achieve puncture without clogging of the sleeve portion. After puncture is achieved, the stylet portion is withdrawn and the bipolar electrode pair inserted through the sleeve portion into the ventricular cavity with the sleeve then being withdrawn so as to leave the bipolar electrode pair in place. In prior art arrangements prior to my U.S. Pat. No. 3,516,412 attending physicians could not readily determine whether proper electrical contact was being achieved inside the cavity. The invention disclosed in my previous U.S. Pat. No. 3,516,412 overcomes this problem of the prior art by providing a linear irregularity close to the end of the bipolar electrode pair which is inserted into the ventricular cavity so as to increase the drag on the electrode as it passes through the sleeve of the inserting needle. This drag ceases abruptly when the portion of the electrode at which the irregularity is located passes out of the needle sleeve. In such an arrangement, simply removing the sleeve portion of the needle places the distal end of the stylet against the endocardium automatically. Moreover, in the arrangement disclosed in my previous U.S. Pat. No. 3,516,412, the cessation of the frictional drag resulting from the linear irregularity exiting the cannula of the needle enables a portion of the bipolar electrode pair between the distal end and the linear irregularity to automtically return to its unbiased or unstressed condition in which an angle is subtended between that portion and the rest of the stylet so as to automatically place the distal end of the stylet against the endocardium.

Although my previous patented arrangement disclosed in U.S. Pat. No. 3,516,412 overcomes several of the problems of the prior art, it still requires the attending physician to first insert the needle into the heart, then remove the inner stylet, thereafter pass the electrode into the sleeve portion, only being able to ascertain or verify entry into the heart by the presence of the aforementioned frictional drag after the bipolar electrode pair has been passed through the inner needle into the patient. Moreover, this arrangement does not readily provide for insertion of a heart stimulating fluid, such as Epinephrin if its use is also desired by the attending physician to assist in restarting the heart function, thus requiring a separate needle puncture or injection. Since in the event of a cardiac arrest time is of the essence, it would be most desirable for the attending physician to have the immediate option of injecting a heart stimulating fluid as well as inserting a bipolar electrode pair with a minimum of effort and time in situations where seconds could mean a patient's life. The prior art, moreover, has been found to be clumsy, especially in emergency situations such as those requiring external chest massage.

These disadvantages of the prior art are overcome by the present invention.

DISCLOSURE OF THE INVENTION

The present invention relates to a bipolar electrode insertion apparatus in which a common needle is employed for selectively placing both a heart stimulating fluid, such as Epinephrin, and a bipolar electrode pair into the heart. Furthermore, the present invention provides for verification of entry into the heart chamber prior to placement of the fluid or bipolar electrode pair into the heart. The apparatus of the present invention includes a syringe capable of injecting the heart stimulating placed therein into the heart chamber or ventricular cavity for restarting the heart function. The needle is a hollow needle having an inlet end and an outlet end for insertion into the heart with a bifurcated chamber being disposed in flow through communication between the syringe outlet end and the needle inlet end. The heart stimulating fluid is selectively injectable into the chamber inlet end through the syringe outlet end and therefrom through the common needle into the ventricular cavity of the heart with the needle inserted therein. The bifurcated chamber contains one branch capable of receiving the fluid from the syringe and another branch comprising an entrance port for a flexible bipolar electrode pair with the entrance port being in flow through communication with the needle inlet end for selective insertion of the bipolar electrode pair through the chamber entrance port into the needle and therefrom through the needle into the ventricular cavity with the needle inserted therein. The flexible bipolar electrode pair has a distal end which is preloaded into the needle and a proximal end extending outwardly through a gasket-type seal at the outer end of the entrance port for enabling the selective insertion of the bipolar electrode pair distal end into the ventricular cavity through the needle outlet end by manipulation of the proximal end of the bipolar electrode pair.

The flexible bipolar electrode pair preferably comprises an inner and an outer electrically conductive element, an insulating element disposed between the inner and outer electrically conductive elements, with the insulating element distal end terminating at a region beyond the distal end of the outer electrically conductive element and short of the distal end of the inner electrically conductive element, and with the outer electrically conductive element being a positive pole comprising at least one coil spring fabricated of a flexible and resilient material, and with the inner electrically conductive element being a negative pole comprising an electrode fabricated of a flexible material. The insulating element proximal end extends beyond the proximal end of the outer conductive element. The distal end of the bipolar electrode pair preferably comprises a flexible bend hook-like portion defined by a short length thereof being disposed in non-alignment with the remaining length thereof when the bipolar electrode pair is in its natural configuration. Preferably, the bend portion comprises the insulating element and the inner electrically conductive element distal ends with the outer electrically conductive element distal end terminating short of the bend portion by a sufficient longitudinal extent so as to require the heart muscle to be involved in the electrical conduction path between the inner and outer electrically conductive elements. An interspace seal, such as an adhesive sealant, such as an epoxy resin, is preferably disposed between the outer electrically conductive element and the insulating element for preventing air leakage when the syringe is used for aspiration, and for preventing fluid leakage upon injection. The chamber and syringe enable rapid verification of entry of the needle into the ventricular cavity due to the subsequent entry of blood through the needle into the chamber upon aspiration by the syringe after injection of the needle and prior to insertion of the bipolar electrode pair and/or stimulating fluid into the ventricular cavity. The above arrangement thus facilitates verification of entry into the ventricular cavity, heart stimulating fluid injection and bipolar electrode insertion with a minimum of effort and time.

BRIEF DESCRIPTION OF DRAWINGS

FIG. 1 is a diagrammatic illustration, partially in section, of a preferred bipolar electrode insertion apparatus in accordance with the present invention;

FIG. 2 is a diagrammatic illustration, partially in section, similar to FIG. 1 showing the apparatus of FIG. 1 with a fluid placed in the syringe;

FIG. 3 is an enlarged fragmentary view of the chamber portion of the embodiments of FIGS. 1 and 2 diagrammatically illustrating verification of entry into the ventricular cavity;

FIG. 4 is a diagrammatic illustration, partially in section, similar to FIG. 2 illustrating insertion of the needle into the heart wall or any portion or organ of the body, with the bipolar electrode pair being inserted into the interior of the heart through the needle;

FIG. 5 is a diagrammatic illustration of the presently preferred bipolar electrode pair employed in the apparatus of FIGS. 1 and 2, with the electrode being preloaded in FIGS. 1 and 2;

FIG. 6 is an enlarged fragmentary view, partially in section, of the bipolar electrode pair of FIG. 5; and FIG. 7 is a diagrammatic illustration of the bipolar electrode pair of the present invention in operating position in the ventricular cavity, and connected to an impulse generator, with the heart muscle being diagrammatically illustrated as being involved in the electrical conduction path between the inner and outer electrically conductive elements of the inserted bipolar electrode pair.

BEST MODE FOR CARRYING OUT THE INVENTION

Referring now to the drawings in detail, and initially to FIG. 1 thereof, the presently preferred embodiment of the bipolar electrode insertion apparatus of the present invention, generally referred to by the reference numeral 20, is shown. As shown and preferred in FIG. 1, insertion apparatus 20 preferably includes a conventional type of syringe portion 22 comprising a cylinder 24 capable of storing a fluid therein for subsequent injection in conventional fashion, and a plunger portion 26 having a rubber stopper 28 at one end thereof, for injecting the fluid stored in the cylinder 24 through an outlet conduit 30 of the cylinder 24. As was previously mentioned, syringe 22 is preferably a conventional syringe and functions in conventional fashion to inject a fluid placed therein through a needle. However, as shown and preferred in FIG. 1, a bifurcated chamber portion 32 is preferably disposed in flow through communication between the syringe 22 and a conventional needle 34 such as a conventional septum penetrating needle or Huber point needle having a non-coring point 36. The conventional needle may preferably be one such as the type commercially available from Popper & Sons, such as an 18 or 19 gTW needle, or any other type of conventional needle so long as the needle is capable of injecting a fluid into the ventricular cavity of the heart from the syringe 22 as well as capable of enabling a bipolar electrode pair, generally referred to by the reference numeral 40, to be selectively inserted or passed into the ventricular cavity through the interior of the needle 34 while, preferably, still enabling injection of the aforementioned fluid through the same common needle 34.

As shown and preferred in FIG. 1, the bifurcated chamber 32 is preferably transparent, such as one made of glass, and preferably includes an in-line branch 42 and an angulated branch 44. As will be explained in greater detail hereinafter, the purpose of the in-line branch portion 42 is to enable visual verification of entry of the needle point 36 into the ventricular cavity. This is accomplished by aspirating with the syringe 22 after injection of the needle 34 which will cause blood to flow back through the needle 34 into the chamber 32 if the needle point 36 has entered the ventricular cavity. This verification is preferably accomplished before insertion of the bipolar electrode pair 40 thereby assuring the attending physician that the insertion apparatus 20 is in the correct position.

The details of the presently preferred bipolar electrode pair 40 will be described in greater detail with reference to FIGS. 5 and 6. Suffice it to say at this time that the bipolar electrode pair 40 preferably includes an outer electrically conductive element 70 and an inner electrically conductive element 72 with an insulating element 74 disposed therebetween whose distal end terminates at a region beyond the distal end of the outer electrically conductive element 70 and short of the inner electrically conductive element 72 distal end. The outer element 70 is preferably the positive pole of the bipolar electrode pair 40 while the inner element is preferably the negative pole. Moveover, suffice it to say that the bipolar electrode pair 40 is preferably flexible and includes a flexible bend hook-like portion 50 at the distal end thereof which hook-like portion 50 facilitates positive contact of the inner electrically conductive element with the interior wall of the heart, as diagrammatically illustrated in FIGS. 4 and 7. As shown and preferred in FIGS. 1 and 2, the bipolar electrode pair 40 is preferably preloaded into the needle 34 so as to facilitate insertion thereof through the needle point 36 in an emergency situation. Since the bipolar electrode pair 40 is flexible, the hook-like distal end portion 50 will substantially straighten out while passing through or being preloaded within the needle 34 interior; however, when exiting the needle 34 the point 36, the resilient hook-like distal end portion 50 will return to its hook-like natural configuration as illustrated in FIGS. 4 and 7. The bipolar electrode pair 40 is preferably inserted into the ventricular cavity by manipulating the proximal end 52 thereof so as to feed the bipolar pair 40 down through a gasket-type seal 54, through chamber 32 via bifurcated portion 44, and therefrom through the interior of the needle 34, out through the point 36 and into the interior of the ventricular cavity as illustrated in FIG. 4. The resiliency of the hook-like portion 50 as it passes through the needle point 36 causes it to contact the interior wall of the ventricular cavity 60. Thereafter, if desired, the needle 34 may be withdrawn from the ventricular cavity solely leaving the bipolar electrode pair 40 in place, as diagrammatically illustrated in FIG. 7. However, as previously mentioned, if desired, a heart stimulating fluid such as Epinephrin may also be injected into the ventricular cavity through the same common needle 34 prior to withdrawal of the needle 34. FIG. 2 illustrates the arrangement of FIG. 1 in which such a heart stimulating fluid 62 has been loaded or placed into the cylinder 24 of the syringe prior to injection thereof. If desired, the bipolar electrode insertion apparatus 20 of the present invention can be prepackaged with such a heart stimulating fluid 62 or it can be provided separately by the user. In addition, the presently preferred bipolar electrode insertion apparatus 20 of the present invention enables the user to have the option of employing the preloaded bipolar electrode pair 40 or injecting a heart stimulating fluid 62, or doing both with the same device and without the necessity of removal or insertion of additional apparatus. Furthermore, as previously mentioned, the same apparatus 20 enables the user to verify insertion into the ventricular cavity without removal of the apparatus 20 and prior to injection of the fluid 62 and/or insertion of bipolar electrode pair 40.

Referring now to FIGS. 5 through 7, the presently preferred bipolar electrode pair 40 configuration is shown. Thus, as shown and preferred in FIGS. 5 through 7, the outer electrically conductive element 70 is preferably an outer electrode fabricated of an extremely flexible and resilient coil spring which is coiled closely around the inner insulated electrode 72. The insulating element 74 may preferably be a polyimide sleeve with the inner electrically conductive element or electrode 72 preferably being a stainless steel cable. It has been found that for a needle, such as a Popper & Sons 19 gTW×5" needle with a non-coring point that a bipolar electrode pair 40 having a 0.010" stainless steel cable inner electrode 72, a 0.012" interior diameter polyimide sleeve insulating element 74 and a 0.025" coil spring outer electrode 70, with a radius of 6 millimeters for the hook-like distal portion 50 may satisfactorily be preloaded into the needle 34 and inserted therethrough into the heart. The gasket-type seal 54 should be sufficiently tight to enable aspiration to be performed while also enabling the bipolar electrode pair 40 to be passed therethrough during insertion of the bipolar electrode pair 40 into the heart as well as preventing air leakage during the aspiration phase. It has been found that a latex plug is a satisfactory type gasket-type seal 54. Moreover, if desired, the coil spring 70 of the bipolar electrode pair 40 may be treated with silicone stopcock grease to facilitate its movement through the latex plug or seal 54. An interspace seal 76, such as an adhesive sealant, such as an epoxy resin, is preferably provided between the insulation 74 and the outer spring 70 so as to prevent any air leakage therebetween which could affect the operation of the syringe 22, such as with respect to aspiration.

As further shown and preferred in FIG. 5, the presently preferred bipolar electrode pair 40 employed with the bipolar electrode insertion apparatus 20 of the present invention preferably longitudinally spaces the distal end 80 of the outer electrode 70 from the exposed or distal end 82 of inner electrode 72 by means of the insulation 74 for a sufficient extent to require the heart muscle to get involved in the electrical conduction path. This feature is diagrammatically represented in FIG. 7 in which the distal end 80 of the outer electrode 70 is shown as terminating either in or adjacent the outer wall of the ventricular cavity 60 while the inner electrode 72 distal end 82 is shown as being adjacent the inner wall of the ventricular cavity 60, with the heart muscle itself completing the electrical conduction path between the inner electrode 72 distal end 82 and the outer electrode 70 distal end 80. As shown and preferred in FIG. 7, the outer electrode 70 is preferably the positive pole which is located within or outside the heart muscle and the inner electrode 72 is the negative pole which is located inside the heart muscle.

Generally, in utilizing the bipolar electrode insertion apparatus 20 of the present invention the needle 34 is passed through the chest wall substantially at the fourth and fifth intercostal space occurring between the ribs of the torso and further passed through the ventricular wall until it enters the ventricular cavity, such as the left ventricle of the heart. Thereafter, the apparatus 20 may be aspirated to verify entry into the ventricular cavity by the subsequent presence of blood in chamber 32. After this verification, if desired, the heart stimulating fluid 62 may be injected into the heart and/or the bipolar electrode pair 40 may be inserted into the ventricular cavity. Upon completion of this insertion, the needle 34 along with the balance of the apparatus 20 except for the bipolar electrode pair 40 is removed. This removal causes the distal end 50 of the bipolar electrode pair 40 to be placed against the endocardium thereby placing the region of highest current density in such a position with respect thereto that the electrical stimulation has the highest probability of successful capture, such as described in my previous U.S. Pat. No. 3,516,412. A conventional impulse generator 90 may then preferably be connected to the inner electrode 72 by lead 92 and to the outer electrode 70 be means of lead 94. Electrical current of the desired strength and frequency may then be applied through the circuit which comprises inner electrode 72, the distal end 82 thereof, the wall 60 of the ventricular cavity, the distal end 80 of outer electrode 70 and the outer electrode 70. With respect to the longitudinal extent of insulating element 74 for spacing the distal end 82 of the inner electrode 72 from the distal end 80 of the outer electrode 70, it has been found that a length of 60 millimeters has been satisfactory.

It should be noted that with respect to the presently preferred bipolar electrode pair 40 to be preloaded into the insertion apparatus 20 of the present invention, that with the exception of the employment of the interspace seal 76 which is relevant to the operation of the insertion apparatus 20 of the present invention, such a bipolar electrode pair 40 has been commercially available from Electro-Catheter Corporation for more than a year, used with a different insertion apparatus having disadvantages. However, such bipolar electrode pair 40, to applicant's knowledge, has only been employed with prior art insertion apparatus which, as previously mentioned, lack the advantages of the apparatus of the present invention, and have never previously been employed in an insertion apparatus such as the insertion apparatus 20 of the present invention.

It is to be understood that the above described embodiment of the invention is merely illustrative of the principles thereof and that numerous modifications and embodiments of the invention may be derived within the spirit and scope thereof, such as by employing other types of flexible bipolar electrode pairs other than that described herein.

What is claimed is:

1. A bipolar electrode insertion apparatus comprising a syringe means capable of injecting a fluid placed therein into the body through an outlet end thereof, a hollow needle, said needle having an inlet end and an outlet end for insertion into the body, a chamber disposed in flow through communication between said syringe outlet end and said needle inlet end, said placed fluid being selectively injectable into said chamber inlet end through said syringe outlet end and therefrom through said needle into the body with said needle inserted in position therein, said chamber further comprising an entrance port for a flexible bipolar electrode means, said bipolar electrode means entrance port being in flow through communication with said needle inlet end for selective insertion of said bipolar electrode means through said chamber entrance port into said needle and therefrom through said needle into the body with said needle inserted in position therein, seal means disposed at said chamber inlet end for selectively isolating said syringe from said chamber, said chamber and needle providing a common conduit into the body for said selectively injectable fluid and said selectively insertable bipolar electrode means.

2. An apparatus in accordance with claim 1 wherein said syringe means comprises means capable of selectively injecting a heart stimulating fluid placed therein through said syringe outlet end, said chamber enabling in situ verification of entry of said needle outlet end into the heart by blood flow thereinto in response to aspiration of said syringe means after insertion of said needle outlet end into the heart.

3. An apparatus in accordance with claim 2 wherein said chamber comprises a bifurcated inlet portion with one of the branches thereof comprising said bipolar electrode means entrance port and the other of said branches comprising said chamber inlet end disposed in flow through communication with said syringe outlet end, said other branch facilitating said verification of entry by said blood flow thereinto.

4. An apparatus in accordance with claim 3 wherein said flexible bipolar electrode means has a distal end preloaded into said needle and a proximal end extending outwardly through said one branch for enabling said selective insertion of said bipolar electrode means distal end into said heart through said needle outlet end by manipulation of said bipolar electrode means proximal end.

5. An apparatus in accordance with claim 4 wherein said flexible bipolar electrode means comprises an inner and an outer electrically conductive element, and an insulating element disposed between said inner and outer electrically conductive elements, said insulating element terminating at a region beyond the distal end of said outer electrically conductive element and short of the distal end of said inner electrically conductive element.

6. An apparatus in accordance with claim 5 wherein said outer electrically conductive element distal end terminates at a sufficient longitudinal extent short of said inner electrically conductive element distal end so as to require the heart muscle to be involved in the electrical conduction path between said inner and outer electrically conductive elements, said insulating element distal end extending for said sufficient longitudinal extent, said inner electrically conductive element distal end extending beyond said insulating element distal end.

7. An apparatus in accordance with claim 6 wherein said inner electrically conductive element comprises an electrode fabricated of a flexible material, said outer electrically conductive element comprising at least one coil spring fabricated of a flexible and resilient material.

8. An apparatus in accordance with claim 7 wherein said bipolar electrode means distal end comprises a flexible bend hook-like portion defined by a short length thereof being disposed in non-alignment with the remaining length thereof when said bipolar electrode means is in its natural configuration.

9. An apparatus in accordance with claim 8 wherein said bend portion comprises said insulating element and inner electrically conductive element distal ends, said outer electrically conductive element distal end terminating short of said bend portion.

10. An apparatus in accordance with claim 5 wherein at least the portion of said preloaded bipolar electrode means resident in said chamber one branch prior to said selective insertion thereof further comprises an interspace sealing means disposed between said outer electrically conductive element and said insulating element for preventing air leakage therebetween.

11. An apparatus in accordance with claim 10 wherein said interspace sealing means comprises an adhesive sealant.

12. An apparatus in accordance with claim 11 wherein said adhesive sealant comprises an epoxy resin.

13. An apparatus in accordance with claim 4 wherein said one branch includes a gasket-type seal at one end thereof, said preloaded bipolar electrode means proximal end extending outwardly through said gasket-type seal, said gasket-type seal sealing said one branch from the ambient environment while enabling said selective insertion therethrough.

14. An apparatus in accordance with claim 13 wherein at least the portion of said preloaded bipolar electrode means resident in said chamber one branch prior to said selective insertion thereof further comprises an interspace sealing means disposed between said outer electrically conductive element and said insulating element for preventing air leakage therebetween.

15. An apparatus in accordance with claim 14 wherein said interspace sealing means comprises an adhesive sealant.

16. An apparatus in accordance with claim 15 wherein said adhesive sealant comprises an epoxy resin.

17. An apparatus in accordance with claim 11 wherein said inner electrically conductive element comprises an electrode fabricated of a flexible material, said outer electrically conductive element comprising at least one coil spring fabricated of a flexible and resilient material.

18. An apparatus in accordance with claim 1 wherein said flexible bipolar electrode means comprises an inner and an outer electrically conductive element, and an insulating element disposed between said inner and outer electrically conductive elements, said insulating element having a distal end terminating at a region beyond the distal end of said outer electrically conductive element and short of the distal end of the inner electrically conductive element.

19. An apparatus in accordance with claim 18 wherein said outer electrically conductive element distal end terminating at a sufficient longitudinal extent short of said inner electrically conductive element distal end so as to require the heart muscle to be involved in the electrical conduction path between said inner and outer electrically conductive elements, said insulating element distal end extending for said sufficient longitudinal extend, said inner electrically conductive element distal end extending beyond said insulating element distal end.

20. An apparatus in accordance with claim 19 wherein said inner electrically conductive element comprises an electrode fabricated of a flexible material, said outer electrically conductive element comprising at least one coil spring fabricated of a flexible and resilient material.

21. An apparatus in accordance with claim 20 wherein said bipolar electrode means distal end comprises a flexible bend hook-like portion defined by a short length thereof being disposed in non-alignment with the remaining length thereof when said bipolar electrode means is in its natural configuration.

22. An apparatus in accordance with claim 21 wherein said bend portion comprises said insulating element and inner electrically conductive element distal ends, said outer electrically conductive element distal end terminating short of said bend portion.

23. An apparatus in accordance with claim 1 wherein said flexible bipolar electrode means has a distal end preloaded into said needle and a proximal end extending outwardly from said chamber for enabling said selective insertion of said bipolar electrode means distal end into the body through said needle outlet end by manipulation of said bipolar electrode means proximal end.

* * * * *